(12) United States Patent
Ripken et al.

(10) Patent No.: US 12,329,689 B2
(45) Date of Patent: *Jun. 17, 2025

(54) AUTOMATIC DARKENING FILTER WITH SIMPLIFIED SET-UP

(71) Applicant: 3M INNOVATIVE PROPERTIES COMPANY, St. Paul, MN (US)

(72) Inventors: Christian A. Ripken, Jüchen-Kelzenberg (DE); Markus Glocker, Neuss (DE)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/495,527

(22) Filed: Oct. 26, 2023

(65) Prior Publication Data

US 2024/0050278 A1 Feb. 15, 2024

Related U.S. Application Data

(63) Continuation of application No. 17/597,571, filed as application No. PCT/IB2020/056225 on Jul. 1, 2020, now Pat. No. 11,813,200.

(30) Foreign Application Priority Data

Jul. 19, 2019 (EP) .................................. 19187291

(51) Int. Cl.
*G02F 1/133* (2006.01)
*A61F 9/06* (2006.01)

(52) U.S. Cl.
CPC .......... *A61F 9/062* (2013.01); *G02F 1/13318* (2013.01)

(58) Field of Classification Search
CPC .......... A61F 9/062; A61F 9/067; A61F 9/065; G02F 1/13318; G02F 1/13306; G02F 1/133528; A42B 3/042
See application file for complete search history.

(56) References Cited

U.S. PATENT DOCUMENTS 4,240,709 A 12/1980 Hornell
7,342,210 B2 3/2008 Fergason
(Continued)

FOREIGN PATENT DOCUMENTS

CN 202933090 U 5/2013
CN 203843345 U 9/2014
(Continued)

OTHER PUBLICATIONS

International Search Report for PCT International Application No. PCT/IB2020/056225, mailed on Sep. 2, 2020, 5 pages.

*Primary Examiner* — Donald L Raleigh
(74) *Attorney, Agent, or Firm* — Aleksander Medved

(57) ABSTRACT

The present disclosure relates to an automatic darkening filter 20 which is suitable for darkening for protection from light, in particular from high intensity light, with a simplified set-up, as well as to a set-up device 40 for setting up parameters of a such filter 20. The present disclosure also relates to a system 100, 100' comprising such an automatic darkening filter 20 and such a set-up device 40, in particular a welding device 110. The present disclosure furthermore relates to a method for setting up such an automatic darkening filter 20 as well as to a headgear 10 with such an automatic darkening filter 20 and to a welding device 110 with such a set-up device 40.

18 Claims, 2 Drawing Sheets

(56) References Cited

U.S. PATENT DOCUMENTS

| | | |
|---|---|---|
| 7,810,937 B2 | 10/2010 | Garbergs et al. |
| 8,047,664 B2 | 11/2011 | Garbergs et al. |
| 8,384,855 B2 | 2/2013 | Sundell |
| 2003/0171054 A1 | 9/2003 | Bansal |
| 2005/0017152 A1 | 1/2005 | Fergason |
| 2010/0328752 A1 | 12/2010 | Garbergs et al. |
| 2013/0291271 A1 | 11/2013 | Becker et al. |
| 2015/0034618 A1 | 2/2015 | Langeder et al. |
| 2015/0209887 A1 | 7/2015 | Delisio |
| 2016/0262467 A1 | 9/2016 | Magnusson et al. |
| 2017/0290707 A1* | 10/2017 | Wu .................. A61F 9/067 |
| 2017/0367891 A1 | 12/2017 | Magnusson et al. |

FOREIGN PATENT DOCUMENTS

| | | | |
|---|---|---|---|
| CN | 104224438 A | 12/2014 | |
| CN | 204379541 U | 6/2015 | |
| CN | 204971843 U | 1/2016 | |
| EP | 3363417 A1 | 8/2018 | |
| WO | 2005009309 A1 | 2/2005 | |
| WO | 2015151050 A1 | 10/2015 | |
| WO | 2015174607 A1 | 11/2015 | |
| WO | 2016001651 A1 | 1/2016 | |
| WO | 2016140384 A1 | 9/2016 | |
| WO | WO-2020034488 A1 * | 2/2020 | ............. A61F 9/067 |

\* cited by examiner

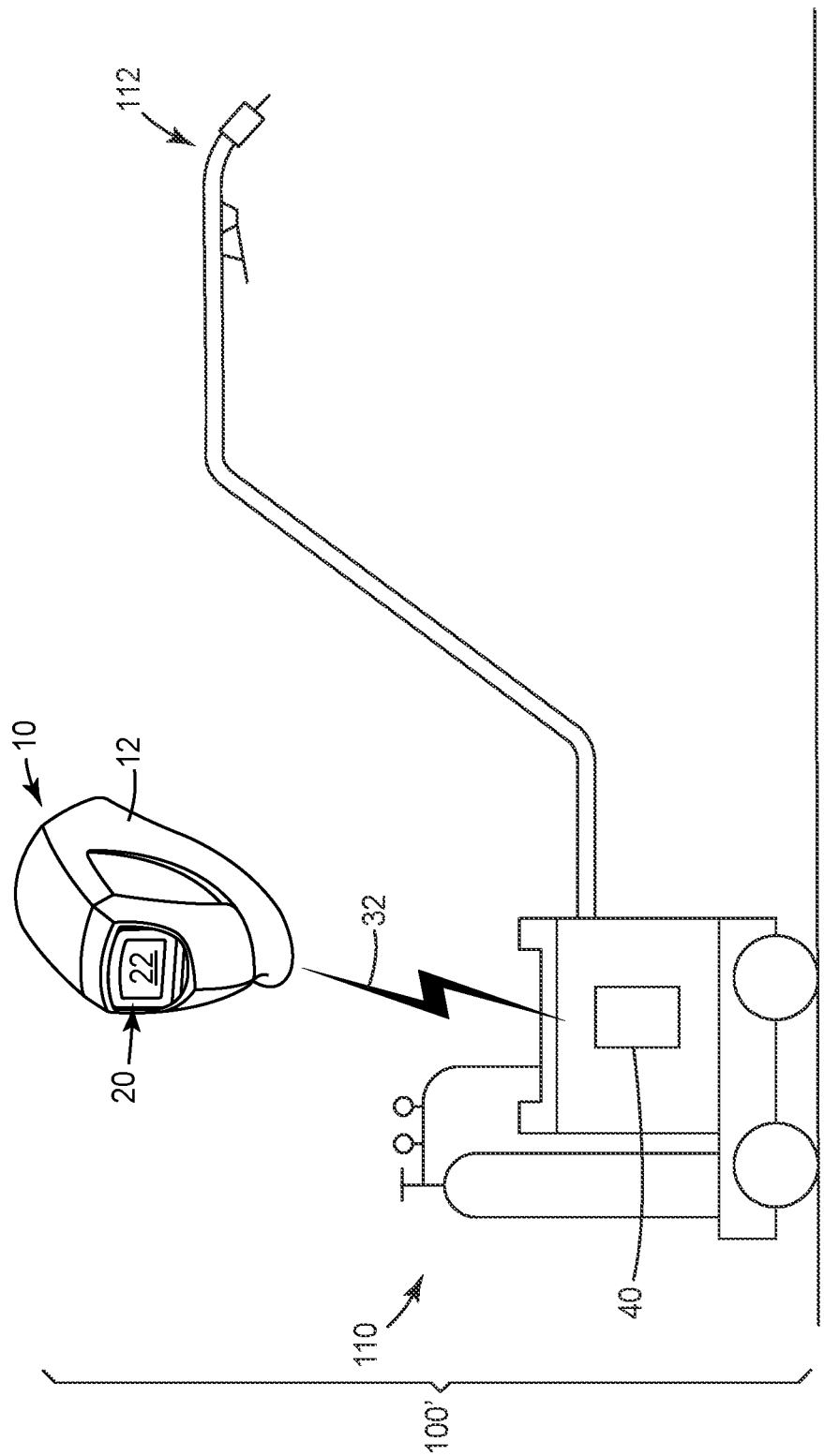

AUTOMATIC DARKENING FILTER WITH SIMPLIFIED SET-UP

TECHNICAL FIELD

The present disclosure relates to an automatic darkening filter (ADF) which is suitable for darkening for protection from light, in particular from high intensity light, with a simplified set-up, as well as to a set-up device for setting up parameters of such a filter. The present disclosure also relates to a system comprising such an automatic darkening filter and such a set-up device. The present disclosure furthermore relates to a method for setting up such an automatic darkening filter as well as to a headgear with such an automatic darkening filter and to a welding device with such a set-up device.

BACKGROUND OF THE DISCLOSURE

Automatic darkening filters are often provided on protective headgears, where protection from high intensity light is desired. Automatic darkening filters commonly have a switchable filter that automatically changes from a light-transmission-state to a dark-transmission-state in response to incident light. The switching is generally achieved through use of a photodetector that is located on, or as part of, personal protective equipment. The photodetector recognizes the presence of the incident light-to-be-filtered, and an electronic module generates a control voltage that, when applied to the switchable filter, causes the filter to change from the light-transmission-state to the dark-transmission-state. Automatic light filters have been designed which contain liquid-crystal cells located between polarizing films. U.S. Pat. No. 4,240,709 to Hornell describes a switchable filter that has a single-twisted, nematic, liquid-crystal cell sandwiched between a pair of mutually crossed polarizers. The liquid-crystal cells are generally flat, optically-transparent, glass substrates that include transparent electrode and alignment layers. The liquid-crystal molecules orientate themselves in a particular direction when a voltage is applied across the liquid-crystal cell under the control of an electronic module. Many commercially available products use this kind of switchable filter. The use of an automatic-darkening filter in a protective shield gives significant ergonomic benefits. Previously, welders, for example, had to "nod" their welding shield down when they struck the welding arc to ensure that their eyes were protected from the torch light. Automatic welding filters eliminated this action since the welding shield could be continuously placed in a down position. As a result, weld pattern quality has been generally improved because more accurate electrode placement can be achieved. Productivity improvements also have been noted since grinding and rework have been correspondingly reduced.

Known welding filters typically have to be set up by adjusting various parameter of the filter such as shade (dark state), sensitivity, delay etc., which depend on different welding conditions and/or individual user preferences. For example, welding of different materials and/or constructions usually requires different set-up of the filter, i.e. differently adjusting the parameters of the filter. Such a set-up was, for example, done by adjusting the respective parameter by a knob on the protective headgear to which the filter is mounted as described, for example, in CN 204971843 U (TECMEN). A disadvantage of such solution was that the user of the filter had to lift and take off the headgear, respectively, in order to operate the knob attached to an outer shell of the headgear for setting up the filter.

As a result of an improvement, it was possible to set up the respective parameter through an external device such as a handheld device being in a wireless communication with the filter as described, for example, in EP 3 363 417 A1 (Optrel) or CN104224438A (Goldland). The user did not have to lift or take off the headgear any longer for adjusting a parameter. However, as several parameters have to be adjusted separately, setting up of the filter may become cumbersome for the user, particularly when frequently changing the welding conditions and/or when wearing protective equipment such as protective gloves.

Therefore, a need exists for a darkening filter with a simplified parameter set up. Also, a need exists to provide a simplified handling of a filter to be set up, particularly when wearing protective gloves etc.

SUMMARY

The present disclosure relates to an automatic darkening filter comprising a switchable filter lens, wherein the switchable filter lens comprises at least one switchable shutter. The switchable filter lens may comprise a frame or housing and may be supported in a headgear such as a welding helmet or welding shield. The switchable filter lens may be replaceable such that the lens can be removed from the headgear and replaced by another or new one. In such a case, the lens may be fixed by a mechanical fastener such as snap-fit etc. Alternatively, the lens may be fixedly arranged on the headgear in a non-replaceable manner, e.g. by an adhesive. The switchable filter lens may have a rectangular shape and may be flat, although other shapes are conceivable such as round, oval, triangular, pentagonal, hexagonal, octagonal or irregular, including curved shapes. The at least one switchable shutter can be switched between at least a light state and a dark state. The filter is configured to be switched according to a predetermined profile. Switching of the filter means switching of the at least one switchable shutter of the switchable filter lens. A filter controller is connected to each of the switchable shutters so as to be able to control switching of each of the shutters. A filter communication unit is connected to the filter controller and is configured to be connected to a set-up device for receiving information about the predetermined profile from the set-up device. The filter controller is configured to associate the predetermined profile with parameters of the filter and to simultaneously adjust at least two of the parameters of the filter. Such a profile may, for example, include parameters like shade (dark status), sensitivity, delay etc. Typically, an automatic darkening filter has sensors to detect light, in particular the arc caused by a worker e.g. when welding. These sensors have a sensitivity which can be adjusted. For example, when detecting a welding arc, the filter should switch from the light to the dark state. However, if other light sources are present, for example, caused by other welders not in the direct viewing area or in a close distance or by warning lamps e.g. from devices or vehicles, such light should not trigger the filter to switch from light to dark state. Therefore, the sensitivity of the sensors can be adjusted to the conditions surrounding the user of the filter. Shade or dark status means how intensive the darkening of the filter lens is supposed to be. This may depend on the welding condition and materials used. Also, only light caused in a certain radius around the user of the filter may be relevant to protect against, if two or more welders are working very close together. This may also have an influence on the setting of the shade. Furthermore, the working current used at the welding machine may influence the shade to be set. The delay means the time after which the filter switches back from dark to light state after disappearance of the light arc. The delay can be adjusted to the surrounding conditions of the welder. For example, when welding thin materials, there is—after finishing the welding step—no or not much light caused by the blaze of the material, against which the filter should protect. In that case no or a very short delay setting is necessary. However, when welding thicker material, substantial light may be caused from the blaze of the material even after disappearance of the welding arc, against which the filter should protect. In that case the delay (filter switch from dark to light state) can be set e.g. between 1 ms and 2 s. For example, the filter controller may simultaneously switch shade and sensitivity or shade and delay or sensitivity and delay. Associating parameters to a predetermined profile is understood to align, for example, a predetermined profile with specific parameters for shade, sensitivity, delay and/or maybe other parameters. Preferably, the filter controller adjusts all of the parameters mentioned above simultaneously. Such a filter is beneficial because it is easier to handle and it is possible to set-up the filter faster. Also, a profile may comprise standard settings for certain working conditions. Thus, setting up the filter according to these standard settings may be advantageous. The safety of the users can be increased because of standard settings, in particular for inexperienced users, for which incorrect settings can thus be avoided with such a filter.

The filter controller is connected to the at least one individual shutter. The filter controller is such connected to each shutter that the filter controller can at least send control signals to individual shutters (i.e. by sending control signals to individual shutters or an array of shutters of a liquid-crystal cell, as discussed earlier herein) to assume any desired state (e.g., light, dark, intermediate, and so on). Two-way communication between the filter controller and the shutters is possible if desired; e.g. the shutters may be configured to send update or confirmation signals regarding the particular state of the shutters at any given time. The filter controller can switch the shutters between various states by use of any convenient control signal; for example, by varying voltages that are applied to the shutters. Upon a change in a control signal being applied by the shutter control system, a shutter may often exhibit a response time in lighter-to-darker transitions of less than one millisecond, and a response time in darker-to-lighter transitions of around a few milliseconds. When a constant value of a control signal is applied, a shutter typically exhibits a relatively constant light transmission.

Each of the individual shutters can switch between at least a light state (in which it is relatively highly light transmissive) and a dark state (in which it is relatively non-transmissive to light). In some embodiments, a shutter can also switch to at least one intermediate state that exhibits a light transmissivity in between of the light state and the dark state. In specific embodiments, a shutter can switch into any of a multiplicity of intermediate states between the light state and the dark state. The term state is meant as a condition of relative light transmissivity, or opacity, of a shutter of an automatic darkening filter.

The amount of incident light transmitted by a shutter in the various states can be characterized in various ways. One way commonly used in the art is the visible light transmission of the shutter. In various embodiments, a shutter is configured so as to exhibit a visible light transmission of less than about 0.5%, less than about 0.1%, or less than about 0.05%, when in a dark state; and, to exhibit a visible light transmission of greater than about 3%, greater than about 10%, greater than about 20%, or greater than about 50%, when in a light state. In various embodiments the visible light transmission of a shutter when in an intermediate state may be less than about 10%, less than about 5%, or less than about 2%, and may be greater than about 0.5%, greater than about 1%, or greater than about 1.5%. Other ranges are possible.

Typically, a switchable shutter comprises a first polarizer, a second polarizer, and a first liquid-crystal cell. The first polarizer has a first polarization direction, and the second polarizer has a second polarization direction. The second polarization direction may be the same or different from the first polarization direction. The liquid-crystal cell is disposed between the first and second polarizers. The liquid crystal cell contains first and second optically transparent, flexible, glass layers and has a liquid crystal layer located between the first and second, optically-transparent flexible glass layers. The first cell may be a twisted, nematic, liquid-crystal cell located (sandwiched) between the first and second polarization filters. As mentioned above, the polarization filters may have substantially orthogonal polarization directions, in which the polarization direction of the first polarization filter is oriented at approximately 90° to the polarization direction of the second polarization filter. These orthogonal polarization directions enable the cell to switch from a light state, and to maintain a light state, when no control voltage is applied to the cell; and to switch to a dark state and to maintain a dark state, when voltage is applied to the cell. More details of such shutters are, for example, described in WO 2018/229688 or US 2016/0262467.

The automatic darkening filter according to the present disclosure further comprises a filter communication unit. The filter communication unit is connected to the filter controller and is configured to be connected to a set-up device for receiving information about the predetermined profile from the set-up device. Such connection may be wireless, e.g. wireless LAN, Bluetooth, Zigbee etc., or wired, e.g. with a cable. Also, an optical connection is conceivable using, for example, a light sensor or a scanner to transfer optical information such as a light signal or an image like a Quick Response (QR) code or bar code to the filter. For example, the filter communication unit receives data from a set-up device and/or transmits data to a set-up device. As mentioned above, such data includes, for example, parameters of a predetermined profile for setting up the automatic darkening filter including shade (dark status), sensitivity, delay etc. Possibly, further data or parameters may be transferred from or to the filter communication unit, for example dark state acknowledge messages, i.e. confirming that the filter has completely switched to the desired dark state. Also, information about the environment of use, for example ambient temperature or humidity, may be transferred as well as information about the working tools with which such a filter may be used, for example a welding machine.

The present disclosure also relates to a set-up device for setting up parameters of an automatic darkening filter according to the present disclosure. The set-up device comprises a set-up communication unit that is configured to be connected to the filter for transmitting a predetermined profile to the filter. The set-up device may further comprise an input device for entering information, e.g. a keyboard, a scanner for scanning bar codes or quick response (QR) codes containing the input information or a light sensor to receive light signals from a light source. Furthermore, the set-up device may also comprise a display for indicating information relevant for setting up the filter. The set-up device may also comprise an interface to which external devices such as a working device, e.g. a welding device, a cutting device or a grinding device can be connected in order to transfer information to the set-up device which is relevant for setting up the filter. The set-up device may also comprise a housing or may be attached to or part of an external working device. Such a set-up device is beneficial because it is easier to handle, and it is possible to set-up the filter faster. In particular, the use of a device separate from the filter prevents the user from lifting the filter for setting it up. Also, standard settings for certain working conditions may be transferred as part of the profile. Thus, setting up the filter according to these standard settings is advantageous because the safety of the users can be increased with the use of standard settings, in particular for inexperienced users, for which incorrect settings can thus be avoided with such a filter.

The present disclosure further relates to a system comprising an automatic darkening filter according to the present disclosure and a set-up device according to the present disclosure. Such a system is beneficial because it is easier to handle, and it is possible to set-up the filter faster. The system uses the advantages as mentioned above for the filter and the set-up device.

The present disclosure moreover relates to a method for setting up an automatic darkening filter according to the present disclosure. The method comprises the steps of providing an automatic darkening filter according to the present disclosure, providing a set-up device according to the present disclosure, establishing a communication between the automatic darkening filter and the set-up device, optionally a wireless communication, transferring a predetermined profile comprising parameters such as shade (dark status), sensitivity and/or delay for setting up of the filter from the set-up device to the filter and setting up the parameters of the switchable filter lens of the filter based on the information received from the set-up device. Such a method is beneficial because it is easier to handle, and it is possible to set-up the filter faster. As mentioned above, the use of the filter and the set-up device according to the present disclosure avoids lifting of the headgear to which such a filter may be attached. Also, standard settings as part of the profile are advantageous to be transferred to avoid incorrect settings of the filter e.g. by inexperienced users.

The present disclosure relates to a protective headgear comprising an automatic darkening filter according to the present disclosure. Headgears may, for example, include welding helmets or welding shields. Such a headgear is beneficial because it provides for a compact design. Also, it is easier to handle, and it is possible to set-up the filter faster. Also, such a headgear makes use of the advantages as listed above for the filter.

The present disclosure also relates to a welding device comprising a set-up device according to the present disclosure. The welding device may send information depending on the welding conditions to the set-up device and thereby translates welding conditions into setting parameters to be sent to the filter. Such a welding device is beneficial because it is easier to handle, and it is possible to set-up the filter faster. Also, such a filter is advantageous because there is a direct data exchange between set-up device and welding device, which provides for further simplification of the use of a welding device with a set-up device and a filter. Also, such a welding device uses the advantages as listed above for the set-up device as this is part of the welding device.

In one embodiment, the communication unit of the filter comprises a wireless receiver and/or optionally a wireless transmitter. The communication unit of the set-up device comprises a wireless transmitter and optionally a wireless receiver. The wireless receiver and/or transmitter may be of the type wireless local area network (WLAN), Bluetooth, Zigbee, radio transmission or the like. Also, optical transmission of information is conceivable, e.g. scanning of bar codes or quick response (QR) codes, visible or infrared light or laser signals etc. Such a wireless receiver and/or transmitter may be beneficial because it replaces a wired connection and gives the user of the filter more flexibility and freedom of movement. It is understood that, alternatively, a wired connection between the filter and the set-up device may be used, e.g. a cable.

In another embodiment, as described above, the predetermined profile transmitted from the set-up device and/or received by the filter comprises parameters of the filter such as shade (dark status), sensitivity, delay and switching information for a warning lamp to indicate the working operation to others in the same environment. Such a predetermined profile with parameters is advantageous because all relevant information for switching the filter is contained in the profile, i.e. the parameters as listed above. Such a profile can be transferred with at least two or all of the parameters at once. Furthermore, specific profiles to be transferred can be created for specific working conditions.

In a further embodiment, the communication unit of the filter is configured to transmit information about the filter to the set-up device. Such information may, for example, include the state to which the filter has been switched, information whether the filter has fully reached the state to which it is supposed to be switched or generally two-way communication including feedback from the filter to the set-up device and/or working device. Such a transmission of information to the set-up device may be beneficial because the user of the filter can view such information on the set-up device without lifting or taking off the filter. Also, the set-up device may further process such information, e.g. documentation of statistic data like time of use, time in light or dark state.

In another embodiment, the set-up device comprises a fastening means for attachment to a working device, such as e.g. a welding device, a cutting device, a grinding device or the like, wherein the fastening means comprises a mechanical fastener such as e.g. a hook & loop fastener, a hook, a snap-fit, a form-fit, adhesive, screws or combinations thereof. Such a fastening means may be beneficial because a secure attachment in a position useful for a user of a filter may be achieved thereby enabling the user to operate the set-up device e.g. through buttons and/or view setting of the set-up device e.g. through a display.

In a further embodiment, the set-up device is configured to be connected to a working device, such as e.g. a welding device, a cutting device, a grinding device or the like. For example, the set-up device may be connected to a welding device such that the set-up device receives information on the welding conditions from the welding device or wherein the set-up device is part of the welding device. Such a connection, e.g. an electrical connection, to a working device may be beneficial as the set-up device may receive information relevant for setting up the filter. Other connections, e.g. an optical connection using visible or IR light, laser, scanning of bar codes or QR codes are conceivable to exchange information between the working device and the set-up device. In case the set-up device is part of the welding device, the working device may directly send information to the filter which is relevant for setting up the filter. Such a set-up device is beneficial as it further reduces complexity of the working device with a set-up device.

In yet a further embodiment, in the system comprising a darkening filter and a set-up device according to the present disclosure the information from or to the set-up device is transmitted wirelessly. Such a wireless transmission of information may be beneficial because it replaces a wired connection and gives the user of the filter more flexibility and freedom of movement.

The invention was described in various embodiments above. It is understood by a person skilled in the art, that one, several or all of the above-mentioned embodiments can be combined with each other.

DETAILED DESCRIPTION

The invention will now be described in more detail with reference to the following Figures exemplifying particular embodiments of the invention:

FIG. 3 is a schematic side view of a protective headgear with an automatic darkening filter according to the present disclosure and a welding device comprising a set-up device according to the present disclosure.

Figure 1:
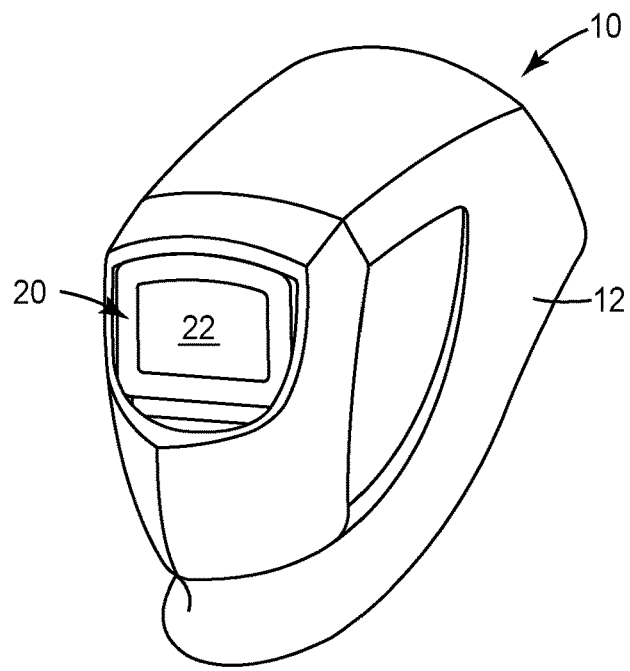
FIG. 1 is a perspective view of a protective headgear, e.g. a welding helmet, that includes an automatic darkening filter (ADF) according to the present disclosure.

FIG. 1 shows an example of a headgear 10 according to the present disclosure, e.g. a welding helmet 10 that includes a helmet body or shell 12 and an automatic darkening filter (ADF) 20. Specifically, the ADF 20 includes a switchable filter lens 22 supported in the helmet shell 12. The switchable filter lens 22 comprises a plurality of switchable shutters 22a, which are not shown in FIG. 1. The switchable filter lens 22 may be mounted in the helmet shell 12 so that it is directly in front of the user's eyes when the helmet is worn by a user. In one embodiment, the switchable filter lens may be replaceable. In the embodiment shown in FIG. 1, the switchable filter lens 22 of the ADF 20 has a substantially rectangular shape. The switchable filter lens 22 may further have a frame or housing, which is not shown in FIG. 1.

Figure 2:
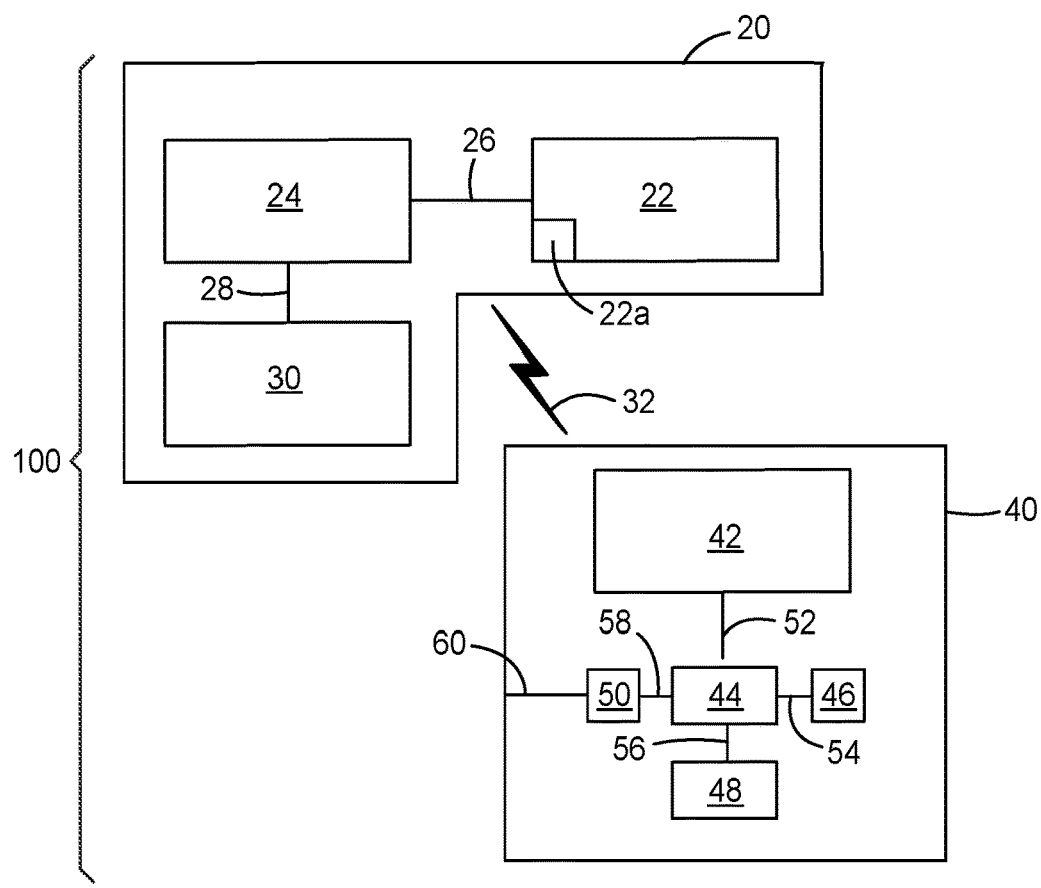
FIG. 2 is a schematic block diagram of an ADF system in which an ADF and a set-up device according to the present disclosure are connected.

FIG. 2 is a schematic block diagram of an automatic darkening filter system 100 including an automatic darkening filter 20 and a set-up device 40 according to the present disclosure. As described above, the ADF 20 comprises a switchable filter lens 22 having a plurality of switchable shutters 22a only one of which is shown in FIG. 2. The switchable filter lens 22 is capable of changing from a light state to a dark state by switching some or each of the switchable shutters 22a from a light state to a dark state, possibly also to at least one intermediate state. The switchable filter lens 22 is electrically connected to a filter controller 24 via connection 26. As outlined above, the filter controller 24 is connected to each of the switchable shutters 22a and is configured to switch the switchable filter lens 22 and the switchable shutters 22a, respectively. The filter controller 24 switches according to a predetermined profile which includes parameters of the ADF, for example shade (dark status), sensitivity and/or delay etc. As describe above, the filter controller 24 may switch two or more, preferably all of the parameters simultaneously. The filter controller 24 is also electrically connected to a filter communication unit 30 via a connection 28. The filter communication unit 30 receives information relevant for switching the switchable shutter 22 of the ADF 20 and transmits this information to the filter controller 24 via connection 28. As can be seen from FIG. 2, the ADF 20 is wirelessly connected to a set-up device 40 as indicated by 32. Such a connection may also be wired, which is not shown in FIG. 2. Other connections, e.g. optical connections including for example a scanner reading a QR code or bar code, light signals etc., are conceivable. The set-up device 40 comprises a set-up device controller 44 which is electrically connected to a set-up communication unit 42 via connection 52. The set-up device controller 44 provides data relevant for switching the ADF 20 to the set-up device communication unit 42, which transmits the received data to the filter communication unit 30, for example wirelessly as indicated by 32 in FIG. 2. Such data either comes from an input device 46 operated by a user of the set-up device 40, wherein the input device 46 is connected to the set-up device controller 44 by connection 54. The input device 46 may for example be a keyboard or a scanner for scanning bar codes or QR codes as input. The data may also come from another device, e.g. a welding device (not shown here), which can be electrically connected to a connection interface 50 via connection 60. The connection interface 50 is in turn electrically connected to the set-up device 40 by connection 58. The set-up controller 44 is also electrically connected to a display 48 via connection 56 for displaying data about the ADF 20 and the set-up device 40, e.g. conditions of the ADF 20 such as the state to which the switchable filter lens is switched, such as parameters of the above-mentioned profile etc. The set-up device 40 and the set-up controller 44, respectively, may also receive information from the filter 20, e.g. a confirmation message that the filter 20 has reached a certain state (dark, light, intermediate). The set-up device 40 may comprise a housing (not shown here) or may be part of another device such as a welding device (not shown here).

FIG. 3 is a schematic side view of an automatic darkening filter system 100' including a protective headgear 10 with an ADF 20 and a welding device 110 comprising a set-up device 40 as part thereof. The welding device 110 may be a welding device 110 for manual metal arc welding (MMA), gas tungsten arc welding (TIG), metal inert gas/metal active gas welding (MIG/MAG) type, plasma welding or with electrodes with or without protective gas. The welding device 110 further comprises a set-up device 40 as described under FIG. 2 above, which is attached to the welding device, preferably such that it forms part thereof. The set-up device 40 is connected to the welding device 110 such that the set-up device 40 receives data from the welding device 110 about the welding conditions. Depending on these welding conditions, the ADF 20 needs to be and will be switched accordingly. The set-up device 40 is wirelessly connected to the protective headgear 10 comprising the ADF 20 as indicated by 32. Other connections, e.g. wired connections, are also conceivable. As described under FIG. 1, the headgear 10 comprises a helmet shell 12, an ADF 20 including a switchable filter lens 22. The switchable filter lens 22 comprises a plurality of switchable shutters 22a, which are omitted here for simplification. The welding device 110 further comprises a welding torch 112 which comprises a push button for operating the welding device 110 including starting or stopping the welding process. A grip intended to allow the operator to handle the welding torch 112 may be provided with the welding torch 112, which is not shown here.

What is claimed is:

1. An automatic darkening filter, comprising:
a switchable filter lens comprising at least one switchable shutter switchable between a first state and a second state;
a filter controller connected to the switchable filter lens to control switching of the switchable filter lens according to a predetermined profile, wherein the filter controller is connected to at least one of the switchable shutters such that the filter controller can: (i) send control signals to the at least one switchable shutter to assume any desired state; and (ii) receive confirmation signals from the at least one switchable shutter regarding the state of the shutter; and
a filter communication unit connected to the filter controller and configured to: (i) receive information from a set-up device of a welding device about the predetermined profile; and (ii) send information to the set-up device regarding the state of the at least one switchable shutter;
wherein the filter is configured to be switched according to the predetermined profile with parameters of the filter.

2. The automatic darkening filter of claim 1, wherein a first state is a light state and a second state is a dark state.

3. The automatic darkening filter of claim 1, wherein the filter controller is configured to adjust at least two parameters of the filter.

4. The automatic darkening filter of claim 3, wherein the at least two parameters of the filter include at least one of shade, sensitivity, and delay.

5. The automatic darkening filter of claim 1, wherein the information from the set-up device includes information about welding conditions.

6. The automatic darkening filter of claim 1, wherein the set-up device includes a set-up communication unit configured to be connected to the filter for transmitting the predetermined profile to the filter.

7. The automatic darkening filter of claim 1, wherein the predetermined profile is configured to be adjusted based on user preference.

8. The automatic darkening filter of claim 7, wherein the predetermined profile is configured to be adjusted manually.

9. The automatic darkening filter of claim 7, wherein the predetermined profile is configured to be adjusted automatically.

10. The automatic darkening filter of claim 1, wherein the predetermined profile is configured to be adjusted during the welding operation.

11. Protective headgear comprising the automatic darkening filter of claim 1.

12. A welding device, comprising:
a set-up device configured to provide information about a predetermined profile and including a set-up device communication unit configured to be connected to an automatic darkening filter for transmitting the predetermined profile to the filter, wherein the set-up device is further configured to receive a confirmation message from the automatic darkening filter that switchable shutters of the automatic darkening filter have reached a certain state,
wherein the filter is configured to be switched according to the predetermined profile with parameters of the filter.

13. The welding device of claim 12, wherein the information from the set-up device includes information about welding conditions.

14. The welding device of claim 12, wherein the set-up device further includes a set-up device controller connected to the set-up device communication unit to provide data relevant for switching the automatic darkening filter to the set-up device communication unit.

15. The welding device of claim 12, wherein the set-up device communication unit is configured to transmit the predetermined profile to the filter wirelessly.

16. The welding device of claim 12, wherein the predetermined profile includes at least two parameters of the filter.

17. The welding device of claim 16, wherein the at least two parameters of the filter include at least one of shade, sensitivity, and delay.

18. The welding device of claim 12 further includes a welding torch, wherein the welding torch includes a button for starting or stopping a welding process.

* * * * *